United States Patent [19]
de la Torre et al.

[11] Patent Number: 5,755,729
[45] Date of Patent: May 26, 1998

[54] MAGAZINE FOR LOADING A NEEDLE AND A LENGTH OF SUTURE ONTO A SURGICAL INSTRUMENT

[75] Inventors: Roger A. de la Torre, Lake St. Louis; James Stephen Scott, St. Charles, both of Mo.; James E. Jervis, Atherton, Calif.

[73] Assignee: General Surgical Innovations, Inc.

[21] Appl. No.: 575,557

[22] Filed: Dec. 18, 1995

Related U.S. Application Data

[63] Continuation-in-part of Ser. No. 429,822, Apr. 27, 1995, Pat. No. 5,630,825.
[51] Int. Cl.⁶ ............................................. A61B 17/00
[52] U.S. Cl. ........................ 606/148; 606/139; 606/144; 112/169
[58] Field of Search ....................... 606/139, 144, 606/145, 146, 147, 148, 151, 205, 207; 112/169, 80.03; 206/338, 339, 438, 63.3, 820

[56] References Cited

U.S. PATENT DOCUMENTS

| 2,910,066 | 10/1959 | Kammer. |
| 5,454,822 | 10/1995 | Schöb et al.. |
| 5,458,609 | 10/1995 | Gordon et al.. |
| 5,472,446 | 12/1995 | de la Torre. |
| 5,478,344 | 12/1995 | Stone et al.. |
| 5,478,345 | 12/1995 | Stone et al.. |

*Primary Examiner*—Jeffrey A. Schmidt
*Attorney, Agent, or Firm*—Howell & Haferkamp, L.C.

[57] ABSTRACT

The present invention pertains to a magazine that is loaded with a needle and an attached length of suture pre-tied in a knot on the magazine. The magazine is used in loading the needle onto a surgical instrument and in loading the tied length of suture onto the surgical instrument.

18 Claims, 5 Drawing Sheets

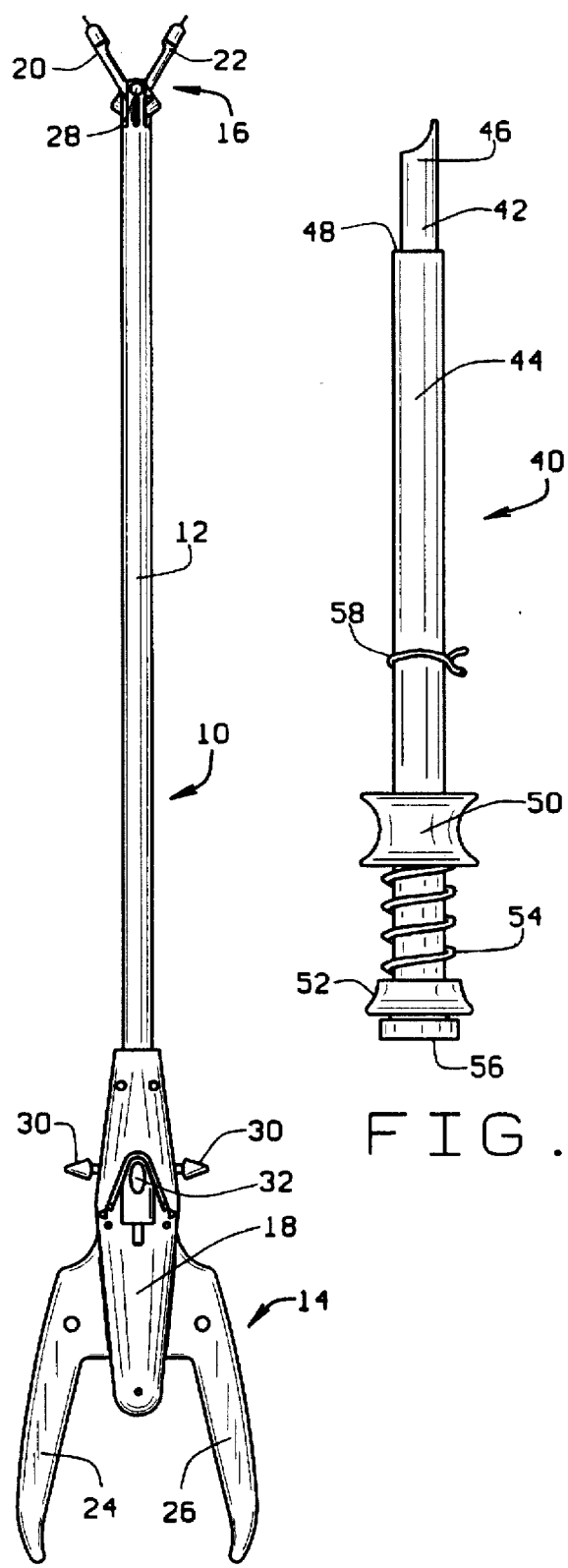
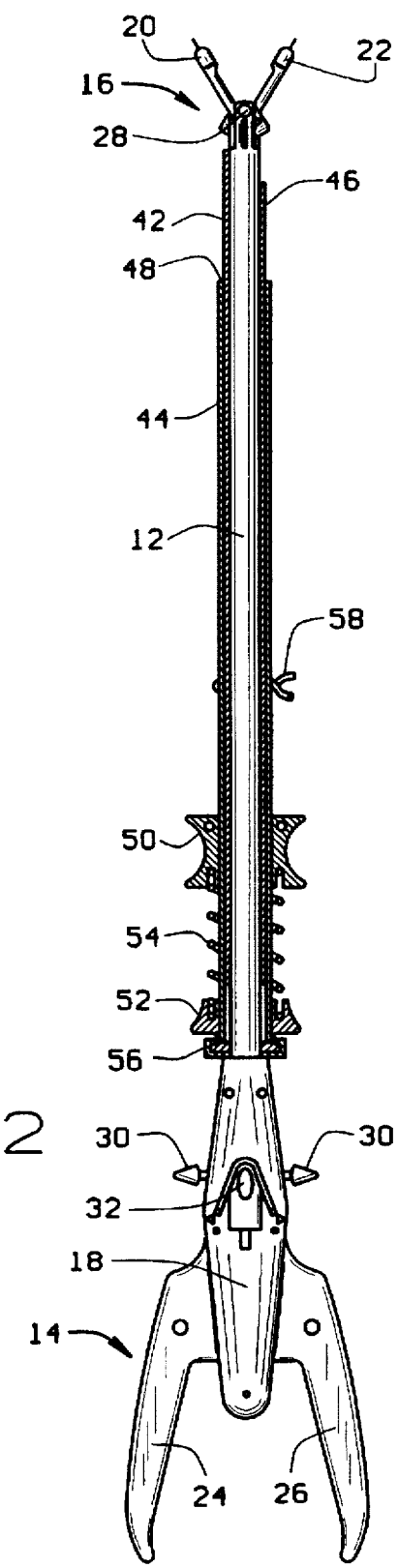
FIG. 1    FIG. 2    FIG. 3

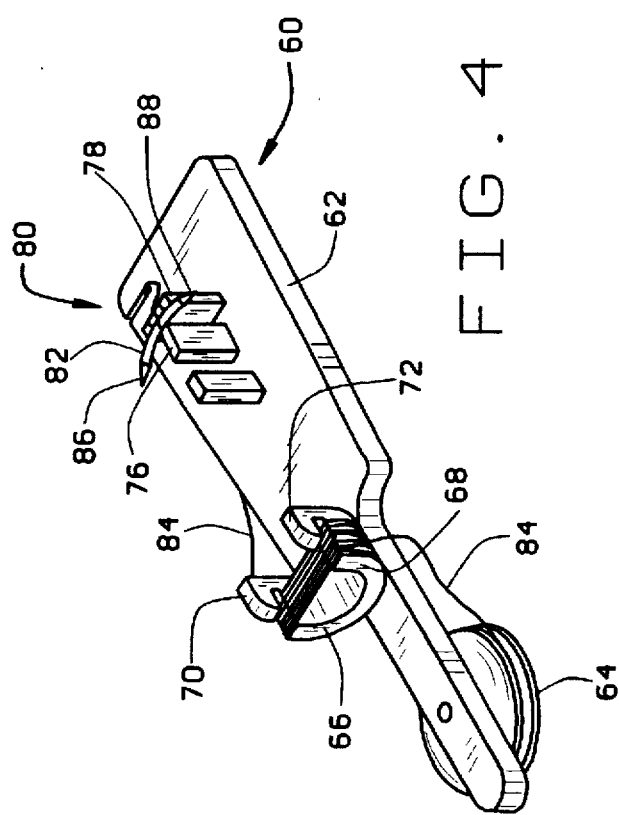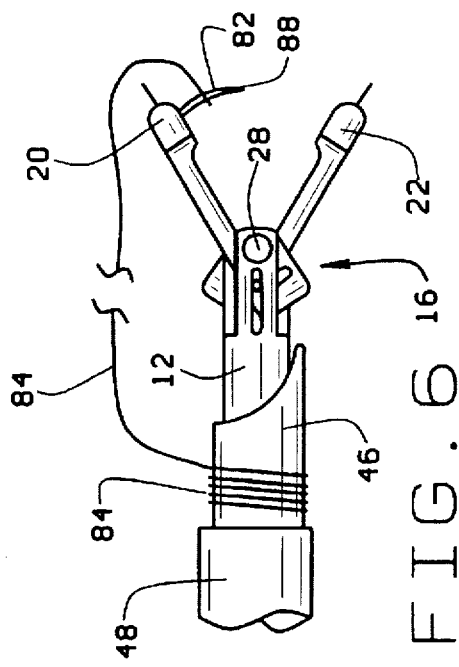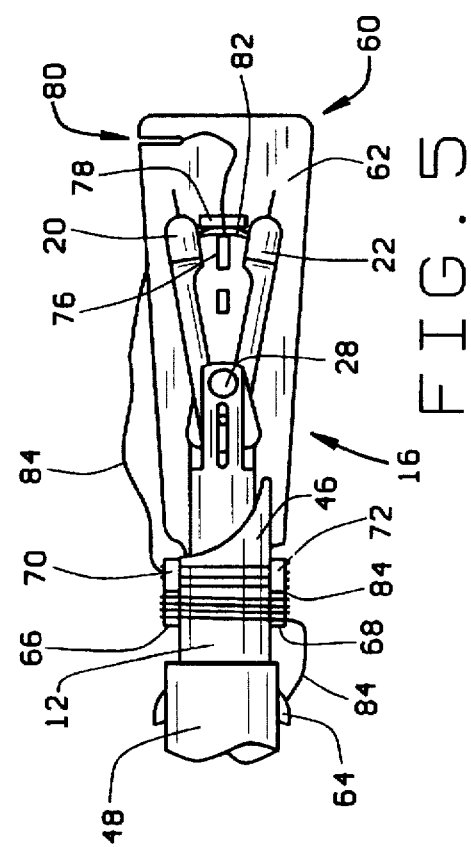

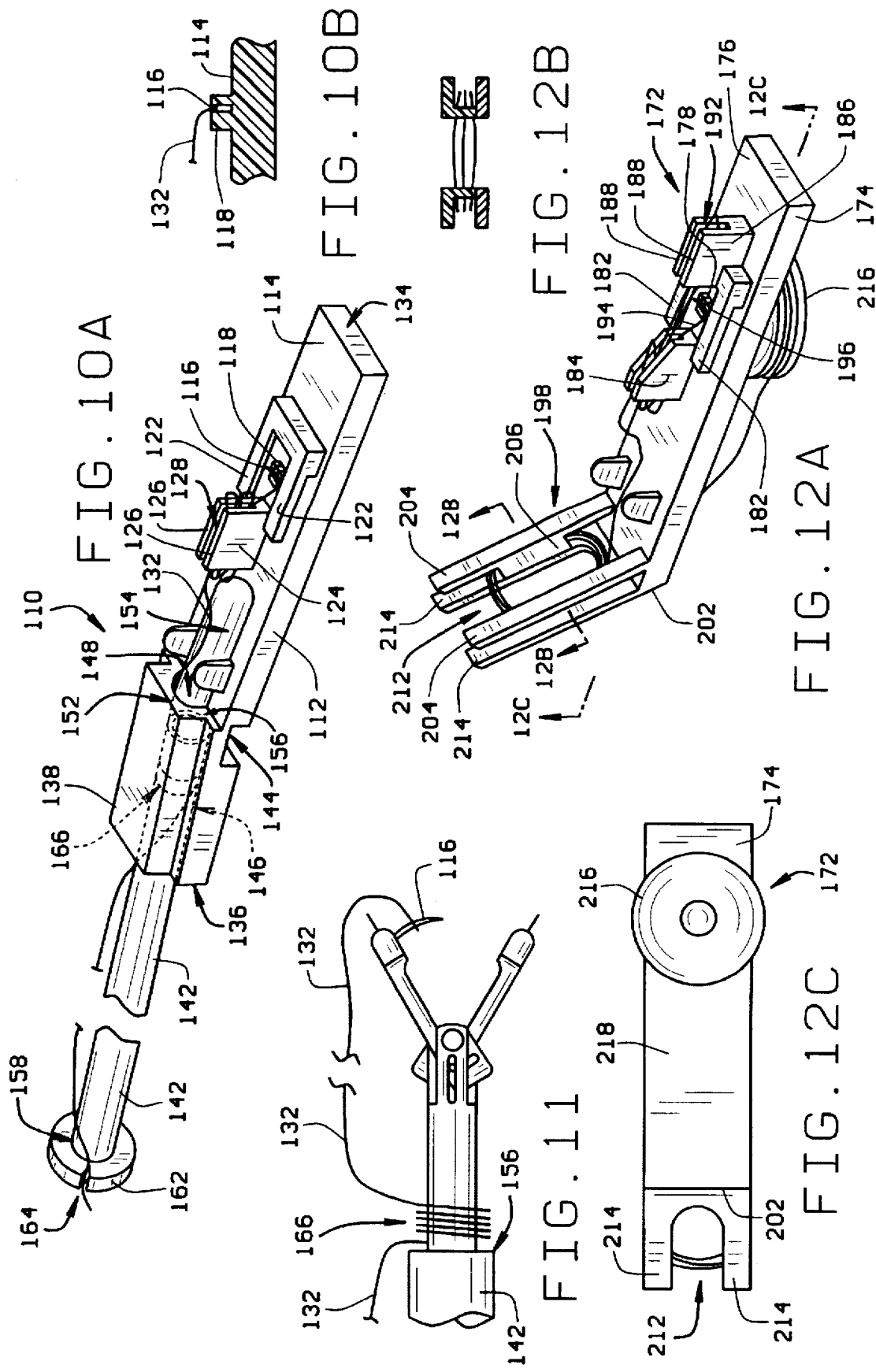

MAGAZINE FOR LOADING A NEEDLE AND A LENGTH OF SUTURE ONTO A SURGICAL INSTRUMENT

This application is a continuation-in-part application of patent application Ser. No. 08/429,822, filed Apr. 27, 1995 and is now U.S. Pat. No. 5,630,825.

BACKGROUND OF THE INVENTION

(1) Field of the Invention

The present invention pertains to a magazine that stores a needle and an attached length of suture pre-tied in a knot on the magazine. The invention also pertains to the method of using the magazine in loading the needle onto a surgical instrument and in loading the tied length of suture onto the surgical instrument.

(2) Description of the Related Art

Various different types of surgical instruments specifically designed for use in minimally invasive surgery are known in the prior art. These instruments are designed for use in laparoscopic surgical procedures where small incisions are made and a remote surgical site within the body is accessed through a cannula inserted through the incision.

One such surgical instrument is the Auto Suture® Endo Stitch® of United States Surgical Corporation. This instrument is comprised of an elongate tube having a pair of opposed handle levers at its proximal end and a pair of opposed arms at its distal end. The pair of arms project from the distal end in a V-shaped configuration in the at rest position of the arms. The surgeon squeezes the opposed handle levers at the instrument proximal end to cause the pair of arms to pivot through arcs toward each other at the instrument distal end. Each of the arms have apertures in their opposing surfaces that contain mechanisms for gripping a needle specifically designed for use with the instrument.

The needle has a slight curvature and tips at its opposite ends. A length of suture is attached to the needle intermediate its ends. When grasping the needle with the instrument, the needle is first positioned between the opposing surfaces of the instrument arms. The handle levers of the instrument are then manipulated toward each other to cause the two arms to pivot through their arc segments toward each other. The points at the needle opposite ends are received into the apertures in the instrument arms as the arms move toward each other. The gripping mechanism in one of the arms grasps the tip of the needle inserted into the aperture of that arm. When the handle levers are released causing the pair of arms to pivot back to their at rest positions where the arms form the V-shaped configuration, the needle remains grasped in the aperture of the one arm. Subsequent manipulation of the instrument handles toward each other will cause the needle to be passed back and forth between the apertures of the two arms with the grasping mechanisms of the two arms alternatively grasping the opposite tips of the needle.

The above-described instrument is specifically designed to be inserted through a cannula and used in placing stitches at a remote location within the body. In use, the body tissue to be stitched is positioned between the arms with the arms in their at rest V-shaped configuration. The handle levers are manipulated toward each other by the surgeon causing the exposed needle tip to pass through the tissue and into the aperture of the instrument arm not holding the needle. That arm then grasps the needle tip inserted into its aperture. The handle levers are then manipulated by the surgeon to cause the arms to return to their at rest, V-shaped positions. This causes the arm now grasping the needle to pull the needle and the attached length of suture through the tissue thereby forming a first stitch in the tissue. The procedure is repeated passing the needle through the tissue and alternatively grasping the needle with the two arms of the instrument. When the number of desired stitches have been placed, the suture ends may be tied off by any of several means. For example, the needle can be cut from the suture and removed and the suture tied in a knot at the surgical location, usually using conventional graspers.

Many prior art instruments have been developed to facilitate tying knots in suture material at surgical sites located in remote areas that are difficult to access. Several of these instruments are specifically designed for use in laparoscopic surgical procedures where the instrument is inserted through a cannula to the surgical site. An example of such an instrument is that disclosed in U.S. Pat. No. 5,391,176, incorporated herein by reference. Other examples of surgical instruments of this type that are specifically designed for tying a knot in a length of suture at a remote location are disclosed in pending U.S. patent applications Ser. No. 08/277,987, filed Jul. 20, 1994, and Ser. No. 08/377,362, filed Jan. 24, 1995, both of which are assigned to the assignee of this application and both of which are incorporated herein by reference. Generally, the knot-tying instruments of this type are comprised of an elongate tube having opposite proximal and distal ends and an interior bore extending through the tube and dimensioned sufficiently large for insertion of another surgical instrument therethrough. The suture-tying instrument is loaded with a length of suture wrapped around its distal end. The length of suture is pre-tied on the distal end of the instrument in one or more knots. A free end of the length of suture extends from the pre-tied knots and is secured to the length of the knot-tying instrument. The opposite end of the length of suture is attached to a needle.

In use of the suture-dispensing instrument, the distal end of the instrument is first inserted through the cannula to position the distal end at the surgical location where it is desired to place one or more stitches in body tissue. The needle is grasped by a separate surgical grasper and passed through the tissue the desired number of times to place the desired stitches. The needle, with the length of suture still attached, is then removed from the surgical site through the interior bore of the knot-tying instrument. The loops of suture wrapped in a knot on the distal end of the instrument are then displaced off the instrument over the length of suture extending from the stitches. The suture extending from the knots is then pulled tight, thereby forming a knot in the suture at the location of the stitches.

Using the Auto Suture® Endo Stitch® in combination with the above-described knot-tying surgical instrument enables the surgeon to easily place a desired number of stitches at a remote surgical location and then tie a knot in the suture. In combination, the interior bore of the knot-tying instrument must be dimensioned sufficiently large to insert the Auto Suture® Endo Stitch® stitching instrument through the interior bore of the knot-tying instrument so that its arms project from the distal end of the knot-tying instrument. The needle with the attached length of suture specifically designed for use with the stitching instrument is then attached to one of the arms of the instrument in the manner described above. However, in order to use these two instruments together taking full advantage of the benefits offered by the two instruments, the length of suture extending from the needle must then be wrapped in a knot on the distal end of the suture-dispensing instrument and the free end of the suture then extended from the knot and secured to the knot-tying instrument.

A magazine apparatus that could be used to quickly load a needle onto the stitching instrument and then load a length of pre-tied suture onto the end of the knot-tying instrument would significantly enhance the benefits provided to the surgeon by these two instruments. Such a magazine could also be used with the stitching instrument alone or with a surgical grasper to load a needle and attached length of suture on these instruments.

SUMMARY OF THE INVENTION

The magazine apparatus of the invention is designed to store thereon a needle of the type used with the Auto Suture® Endo Stitch® stitching surgical instrument of United States Surgical Corporation, together with a length of suture attached to the needle. It may also be used with a conventional surgical grasper. Therefore, "surgical instrument" or "stitching instrument" as used herein should not be interpreted as limited to any particular instrument. The apparatus stores the length of suture in one or more pre-tied knots on the apparatus. Using the apparatus in practicing the method of the invention, the needle and attached length of suture are loaded onto the stitching instrument and a knot-tying instrument through which the stitching instrument has been inserted. The needle is loaded onto one of the two arms of the stitching instrument and the length of suture tied in one or more knots is loaded onto the distal end of the knot-tying instrument.

In various embodiments of the magazine apparatus of the invention, the needle is supported on the magazine with its opposite tips exposed so that it can be easily grasped at one of its tips by the arms of the stitching instrument. In embodiments of the magazine, it is provided with a pair of opposed sidewalls or arms around which the suture is wrapped in at least one knot. In further embodiments of the magazine, the magazine is formed with a tubular portion around which the length of suture is wrapped in at least one knot. Some of the embodiments also include a spool or bobbin around which is wrapped an additional length of suture leading to the free end of the suture.

In use, the stitching instrument is first inserted through the center bore of the knot-tying instrument so that the arms of the stitching instrument project from the distal end of the knot-tying instrument. The stitching instrument handle levers are operated by the surgeon to pivot the pair of arms of the instrument to their mutually opposed, adjacent positions. The arms of the instrument are then inserted through the magazine opposed sidewalls or magazine tubular portion, and thereby the arms are inserted through the knot wrapped in the suture around the magazine. The arms of the stitching instrument are then caused to move to their V-shaped, at rest positions by manipulating the handle levers of the instrument. The arms are next moved adjacent the needle held on the magazine so that the needle is positioned between the apertures of the two arms. Again, the handle levers of the instrument are manipulated to cause the two arms to move toward each other, thereby gripping one of the tips of the needle in the apertures of the two arms.

Next, the knot tied in the suture around the magazine is slipped off an end of the magazine and onto the distal end of the knot-tying instrument. The needle is then pulled from the magazine while held between the two arms of the stitching instrument, thereby completing the loading of the knot tied in the suture on the knot-tying instrument and the loading of the needle connected to the suture on the stitching instrument. The free end of the suture is then anchored near the proximal end of the knot-tying instrument.

In the embodiment of the magazine having opposed sidewalls, the above-described loading of the suture on the knot-tying instrument and the needle on the stitching instrument completely disconnects the magazine from these two instruments. In embodiments of the magazine having a tubular portion around which the knot in the suture is wrapped, after the suture knot is loaded on the knot-tying instrument and the needle loaded on the stitching instrument, the tubular portion of the magazine is slipped over the ends of these two instruments to disconnect the magazine from the instruments and complete the loading of the suture and needle.

In a still further embodiment of the magazine of the invention, the stitching instrument and knot-tying instrument are inserted into a tubular portion of the magazine and the knot tied in the suture around the tubular portion is slipped off the magazine onto the knot-tying instrument. The two instruments are then removed from the tubular portion of the magazine and the magazine is turned 180 degrees to present the needle to the stitching instrument. The arms of the stitching instrument are then manipulated as described above to grip the needle between the two arms. The needle is then pulled from the magazine, thereby disengaging the magazine from the instruments and completing the loading of the suture and needle on the instruments.

In further embodiments, the needle and suture are loading directly on a surgical instrument to be used in placing stitches, without employing a knot tying instrument.

BRIEF DESCRIPTION OF THE DRAWINGS

Further objects and features of the invention are revealed in the following detailed description of the preferred embodiments of the invention and in the drawing figures wherein:

FIG. 1 shows the Auto Suture® Endo Stitch® stitching surgical instrument;

FIG. 2 shows the knot-tying surgical instrument;

FIG. 3 shows the stitching instrument of FIG. 1 inserted through the center bore of the knot-tying instrument of FIG. 2;

FIG. 4 is a perspective view of a first embodiment of the suture and needle loading magazine of the invention;

FIG. 5 is a partial view of the magazine loading a length of suture and a needle on the stitching instrument and knot-tying instrument of FIGS. 1 and 2;

FIG. 6 is a partial view of the length of suture and needle loaded onto the stitching instrument and knot-tying instrument of FIGS. 1 and 2;

FIGS. 9–13 show further embodiments of the magazine of the invention.

DESCRIPTION OF THE PREFERRED EMBODIMENTS

Figure 7:
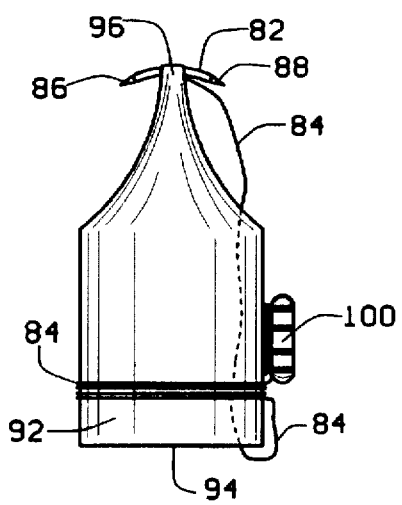
FIGS. 7 and 8 show a further embodiment of the magazine of the invention.

The magazine of the invention is specifically designed to store a needle and attached length of suture and to be used, according to the method of the invention, to load the needle onto a surgical instrument and to load the length of suture onto the surgical instrument. The surgical instrument is not a part of the magazine of the invention or the method of using the magazine. The magazine of the invention is designed for use with a stitching instrument and knot-tying instrument of the types disclosed in U.S. patent application Ser. No. 08/429,822 to facilitate the loading of the needle on the stitching instrument and the attached length of suture on the knot-tying instrument. However, the magazine is equally well-suited for loading a needle and length of suture on the stitching instrument alone or on a surgical grasper or other type of laproscopic instrument. The description of the first embodiments of magazine to follow is with reference to a particular stitching instrument and a particular knot-tying instrument. It should be understood that the description with reference to these two particular instruments is for illustrative purposes only and is not intended to be limiting. The magazine of the invention may be used with other similar types of stitching and knot-tying surgical instruments than those described herein. Additional embodiments of the magazine will be described as being used with the stitching instrument alone or with a surgical grasper. Various embodiments of the magazine of the invention are shown in the drawing figures. However, to understand why these magazines are designed in the way they are and how these magazines are used, it is first necessary to understand the construction and function of the stitching instrument and knot-tying instrument with which the magazine is used.

In FIG. 1 is shown the Auto Suture® Endo Stitch® stitching surgical instrument 10 of United States Surgical Corporation. Because this instrument is known in the prior art, its construction and operation will be described herein only generally.

The stitching instrument 10 has a longitudinally, elongated tubular body 12 with opposite proximal 14 and distal 16 ends. The proximal end 14 of the body has a handle assembly 18 mounted thereon. The distal end of the body has a pair of arms 20, 22 mounted thereon for pivoting movement relative to the body. A pair of hand levers 24, 26 on the handle assembly 18 manipulate the arms 20, 22. The hand levers and arms are shown in their at rest positions in FIG. 1. By manipulating the hand levers 24, 26 toward each other by squeezing the levers, the pair of arms 20, 22 are caused to pivot about the pivot pin 28 through arc segments moving the two arms toward each other so that they are positioned substantially parallel to the longitudinal axis of the instrument body 12. Releasing the squeeze on the hand levers 24, 26 causes the levers to move apart from each other and causes the arms 20, 22 to pivot back through the arc segments to their at rest positions shown in FIG. 1. A spring mechanism contained within the instrument causes the arms to return to their at rest positions.

A pair of lock tabs 30 are provided on the handle assembly 19. The lock tabs 30 are moved downwardly as viewed in FIG. 1 when the hand levers 24, 26 are squeezed toward each other to lock the arms 20, 22 in their mutually opposed, parallel positions. A release button 32 is also provided on the handle assembly 18. The release button 32 is pressed when the arms 20, 22 are in their locked, parallel positions to release the arms.

Although not shown in FIG. 1, the arms 20, 22 have small apertures in their mutually opposed surfaces. The apertures are dimensioned to receive therein a point of a needle specifically designed to be used with the stitching instrument. The needle has a slight curvature and has points at its opposite ends. When the arms are operated by manipulating the hand levers 24, 26 to move the arms toward each other through their arc segments, positioning the needle between the arms will result in the opposite tips of the needle being received in the two apertures of the arms. A mechanism is provided in each arm to alternately grip the opposite tips of the needle in one of the arms when the arms are manipulated between their closed positions and their at rest positions. This enables the stitching instrument 10 to pass the needle between the two arms 20, 22 as the hand levers 24, 26 are operated.

The knot-tying instrument 40 shown in FIG. 2 is one of the embodiments of knot-tying instruments disclosed in U.S. patent application Ser. No. 08/277,987, filed Jul. 20, 1994, and U.S. patent application Ser. No. 08/377,362, filed Jan. 24, 1995, both of which are assigned to the assignee of the present invention and both of which are incorporated herein by reference.

Generally, the knot-tying instrument 40 is comprised of an inner tubular member 42 and an outer tubular member 44. The inner tubular member has a hollow interior bore dimensioned sufficiently large to permit the insertion of the stitching instrument 10 therethrough. The longitudinal length of the inner tubular member 42 is smaller than that of the body 12 of the stitching instrument so that the distal end 16 of the stitching instrument projects from the distal end 44 of the inner tubular member when the instrument is inserted through the tubular member. The longitudinal length of the inner tubular member 42 is slightly smaller than that of the outer tubular member 44 so that only a knot-pushing projection 48 on the distal end of the inner member will extend out of the distal end 48 of the outer member when the inner member is completely retracted into the outer member.

A handle 50 is mounted for reciprocating movement over the exterior of the outer tubular member 44. The handle 50 is connected through longitudinal slots (not shown) in the outer tubular member 44 to the inner tubular member 42 so that the inner tubular member reciprocates within the outer tubular member in response to the handle being reciprocated over the exterior of the outer tubular member. An end cap 52 is secured to the proximal end of the outer tubular member 44 and a spring 54 is positioned between the end cap 52 and the handle 50. The spring 54 biases the handle 50 and the inner tubular member 42 to their extended positions shown in FIG. 2. A seal 56 having a center aperture is secured over the end cap 52 to effect a seal to the stitching instrument.

In operation of the knot-tying instrument 40, a length of suture is first wrapped over the distal end 46 of the inner tubular member. The length of suture is wrapped in a pattern that will produce a knot in the suture when one end of the suture, having a needle attached thereto, is inserted through the center bore of the inner tubular member 42 from its distal end 46 and the knot wrapped in the suture on the inner member distal end 46 is pushed off the member and onto the length of suture extending into the member interior bore. To push the knot formed on the inner member distal end 46 off the end, the handle 50 is manipulated toward the end cap 52 against the bias of the spring 54. This causes the inner member distal end 46 to be retracted into the outer member 44 so that only the knot-pushing projection extends from the outer member distal end 48. The movement of the outer member distal end 48 over the inner member distal end 46 pushes the knot off of the inner member and onto the length of suture drawn into the interior bore of the inner member.

FIG. 3 shows the relative positions of the stitching instrument 10 and knot-tying instrument 40 when the stitching instrument has been inserted through the interior bore of the knot-tying instrument. In these relative positions of the two instruments, the magazine of the invention may be used according to the method of the invention to load a needle onto one of the arms 20, 22 of the stitching instrument while loading a length of suture attached to the needle and tied in one or more knots onto the inner member distal end 46 of the knot-tying instrument 40.

FIG. 4 shows a first embodiment of the magazine 60 of the invention. In the preferred embodiment, the magazine is constructed entirely of plastic. However, other materials may also be employed. The magazine is comprised of a base 62 having a longitudinal length and a lateral width. At one end of the longitudinal length of the base is a spool 64 secured to the bottom surface of the base for rotation relative to the base. The spool 64 is employed in storing a length of suture as will be explained. Projecting from the top surface of the base intermediate its longitudinal length is a means for holding a length of suture comprised of a pair of sidewalls or projections 66, 68. As best seen in FIG. 4, the projections 66, 68 come together forming a U-shaped channel which is spaced slightly above the top surface of the base. The U-shaped channel positions the projections 66, 68 sufficiently far apart to enable insertion of the distal end of the stitching instrument 10 therethrough. Each of the projections, 66, 68 has a block 70, 72 respectively, formed at its top end. The blocks 70, 72 prevent suture wrapped around the projections from being pushed off of the projections as the stitching instrument 10 is inserted between the projections and through the suture wrapped around the U-shaped channel formed by the projections.

Spaced longitudinally from the projections 66, 68 on the top surface of the base 62 is a means for holding a needle on the base in the form of a pair of needle projections 76, 78. As seen in FIGS. 4 and 5, the needle projections 76, 78 are arranged in a T-shaped configuration with a slight spacing between the two projections. The spacing is dimensioned sufficiently small to wedge the needle between the projections 76, 78. The lateral width dimensions of the needle projections 76, 78 are sufficiently small so that the tips at the needle opposite ends project laterally beyond the two projections.

The base 62 is also provided with a small slot 80 in its side. The slot 80 is provided for insertion of the suture therein to keep the portion of suture extending from the needle to that wrapped around the projections 60, 68 from hanging loose from the magazine.

Shown in FIGS. 4–6 is a needle 82 with attached length of suture 84 of the type employed with the stitching instrument 10. As explained earlier, the needle 82 has tips 86, 88 at its opposite ends and is formed with a slight curvature. The suture 84 is secured to the needle intermediate its opposite tips. The needle 82 is secured to the magazine 60 by being wedged in the space between the needle projections 76, 78. As seen in FIGS. 4 and 5, the needle is secured between these projections at the intermediate portion of the needle so that its opposite tips 86, 88 project laterally from the projections and are readily accessible.

The suture 84 extends from the needle through the slot 80 and then beneath the base 62 to the pair of projections 66, 68 above the top surface of the base. The suture is then wrapped around the U-shaped channel formed by the projections 66, 68 in a pattern of loops that will form a knot in the suture when the needle 82 is inserted through the pattern of loops. There are a variety of different patterns of loops of suture material that may be formed around the projections 66, 68 to produce a knot in the suture when the needle is inserted through the pattern of loops. Several examples of such loop pattern are disclosed in U.S. patent application Ser. No. 08/277,987 and Ser. No. 08/377,362, referred to earlier. From the pattern of loops wrapped around the projections 66, 68, the suture then extends to the spool 64 where the remaining length of suture extending to its free end is wrapped around the spool.

The use of this first embodiment of the magazine 60 according to the method of the invention is illustrated in FIGS. 5 and 6. With the stitching instrument 10 inserted through the center bore of the knot-tying instrument 40, the hand levers 24, 26 of the stitching instrument are manipulated to cause the arms 20, 22 to move through their arc segments to their mutually opposed, parallel positions. The arms are then either held in this position or locked in position by engaging the lock tabs 30 on the stitching instrument. The arms are then inserted through the U-shaped channel formed by the pair of projections 66, 68 and through the pattern of suture loops wrapped around the projections. Once the arms have cleared the suture loops, the handle levers are released or the release button 32 is pressed to cause the arms to be biased to their at rest positions. The stitching instrument and knot-tying instrument are then together inserted further through the projections 60, 68 and the pattern of loops so that the distal end 46 of the knot-tying instrument inner tubular member is inserted between the projections 66, 68 and the pattern of suture loops wrapped around the projections. With this positioning of the inner tubular member distal end 46 relative to the projections 66, 68, the pair of arms 20, 22 of the stitching instrument are positioned on opposite sides of the needle 82 held by the magazine.

The handle levers 24, 26 of the stitching instrument are then squeezed together to cause the arms to pivot toward each other and receive the opposite tips 86, 88 of the needle in their apertures as shown in FIG. 5. The arms are then locked by engaging the lock tabs 30 or the surgeon continues squeezing the hand levers 24, 26 so that the arms 20, 22 hold the needle 82 between their opposed surfaces as shown in FIG. 5. The base 62 of the magazine is then pivoted downwardly from the arms thereby pulling the needle 82 from the spacing between the needle projections 76, 78. The arms are then unlocked and the hand levers 24, 26 are permitted to move away from each other to their at rest positions causing the arms 20, 22 to pivot away from each other to their at rest positions. This results in the needle being held at one of its tips in one of the arm apertures.

Next, the pattern of loops wrapped around the projections 66, 68 is pushed off the projections in a direction away from the blocks 70, 72 and onto the inner tubular member distal end 46 of a knot-tying instrument. This loads the pattern of loops on the knot-tying instrument.

The magazine 60 is then moved toward the proximal ends of the stitching instrument and knot-tying instrument causing a length of suture to be pulled from the spool 64. As the length of suture is pulled from the spool, it pulls tight the knot formed in the suture around the inner tubular member distal end 46 of the knot-tying instrument. The length of suture is wrapped around the cleat 58, and then the suture is cut, freeing the magazine 60 from the suture and completing the loading of the needle and suture on the two instruments from the magazine.

Figure 8:
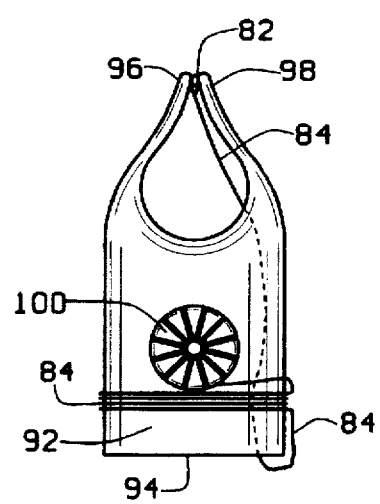

FIGS. 7 and 8 show a further embodiment of the magazine of the invention. In this embodiment, the base 92 has a tubular configuration at its proximal end 94. The base has a hollow interior bore that extends entirely through its longitudinal length. The interior bore is dimensioned sufficiently large to pass the pair of arms 20, 22 of the stitching instrument therethrough with the arms holding the needle 82 between them. The tubular portion of the base adjacent its proximal end 94 functions as the opposed projections 66, 68 of the previously described embodiment as will be explained. In this embodiment, the opposed projections form opposite sides of the tubular portion. As the base extends longitudinally, its configuration changes from tubular to a pair of opposed needle projections 96, 98. As the needle projections extend longitudinally from the tubular portion of the base, they taper toward the center axis of the tubular portion. At the distal ends of the needle projections 96, 98 there is a spacing between the projections dimensioned sufficiently small to wedge the needle 82 therein.

A spool 100 is mounted to the exterior of the base 92 for rotation of the spool relative to the base.

As in the previously described embodiment, the needle 82 with the attached length of suture 84 is mounted and stored on the base 92 of the magazine embodiment of FIGS. 7 and 8. As shown in the drawing figures, the needle 82 is wedged at an intermediate portion of the needle into the spacing between the distal ends of the needle projections 96, 98. The opposite tips 86, 88 of the needle project laterally beyond the needle projections where they can be easily grasped between the arms 20, 22 of the stitching instrument.

The suture 84 extends from the needle 82 through the interior bore of the base 92. The suture emerges from the bore at the proximal end 94 of the base and is wrapped in a pattern of loops around the exterior of the base adjacent its proximal end. As in the previously described embodiment, the pattern of suture loops will produce a knot in the suture when the needle is passed through the center of the loops once mounted on the knot-tying instrument 40. From the pattern of loops, the free end of the suture extends to and is wrapped around the spool 100.

The use of the embodiment of the magazine shown in FIGS. 7 and 8 is similar to the previously described embodiment. Together, the distal ends of the stitching instrument and knot-tying instrument are inserted through the interior bore of the base from its proximal end 94. The arms 20, 22 of the stitching instrument are held in their mutually opposed, parallel positions as they are inserted through the interior bore of the base. As the arms approach the distal ends of the needle projections 96, 98, the hand levers 24, 26 of the stitching instrument are manipulated to cause the arms to pivot open to their V-shaped, at rest configurations. The arms are then positioned on the opposite sides of the needle 82 with the apertures of the arms adjacent the opposite needle tips 86, 88. The hand levers are then again manipulated causing the arms to pivot toward each other and thereby engaging the needle tips 86, 88 in the apertures of the arms.

Next, the pattern of loops of suture 84 is slipped off of the base proximal end 94 onto the distal end 46 of the knot-tying instrument inner tubular member. The stitching instrument 10 and knot-tying instrument 40 are then removed from the interior bore of the base 92. The base is then moved along the longitudinal length of the knot-tying instrument to the cleat 58 while the length of suture wrapped around the spool 100 unwinds from the spool. The length of suture is then secured to the cleat 58 and cut, thereby releasing the magazine embodiment of FIGS. 7 and 8 from the two instruments and completing the loading of the needle and length of suture on the instruments.

Figure 9:
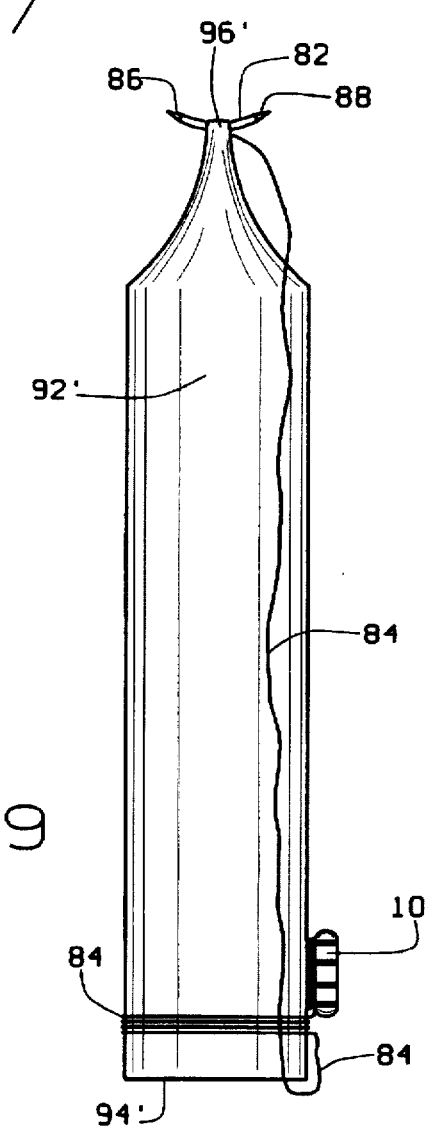

The embodiment of FIG. 9 is similar to that of FIGS. 7 and 8 and like component parts have the same reference numbers followed by a prime ('). The only difference in the FIG. 9 embodiment of the magazine is that its longitudinal length is extended. The larger length of the base makes it easier to handle. Also, the needle 82 is held on the base in an opposite orientation to the base than that of the previous embodiment so that the needle may be grasped by the stitching instrument from outside the tubular interior of the base. This also requires that the suture extend outside the base from the needle 82. As shown in FIG. 9, the projections 96' hold the needle 82 at an intermediate portion of the needle with the needle opposite tips 86, 88 projecting laterally outward from the pair of projections. The length of suture 84 extends from the needle along the exterior surface of the base 92' and is wrapped in a pattern of loops adjacent the base proximal end 94'. From the pattern of loops the free end of the suture is wrapped around the spool 100'.

In use, the needle 82 is first gripped between the arms 20, 22 of the stitching instrument without inserting the instruments through the interior bore of the base 92'. With the needle gripped between the stitching instrument arms, the distal ends of the two instruments are then inserted through the base interior bore from the base proximal end 94'. The pattern of wrapped suture loops is then slipped off the base proximal end 94' and onto the distal end 46 of the knot-tying instrument inner tubular member. The base is then removed from the distal ends of the instruments and moved along the length of the two instruments toward the cleat 58 on the knot-tying instrument and the free end of the suture is wrapped around the cleat. The suture is then cut free from the two instruments, thereby completing the loading of the needle and length of suture on the instruments.

FIGS. 10A and 10B show a further embodiment of the magazine 110 of the invention. As in previous embodiments, the magazine includes a base 112 having a longitudinal length and a lateral width. Projecting from the top surface 114 of the base is a means for holding a needle 116 on the base above the top surface. This includes a needle mount 118 comprised of a pair of projections that extend outwardly from the base top surface 114. The pair of needle mount projections 118 have a lateral width that is smaller than the length of the needle. This causes the opposite ends of the needle to project outwardly from the opposite lateral ends of the needle mount 118 when the needle is received in the mount. This enables either of the opposite ends of the needle to be grasped while the needle is held in the needle mount 118. A small opening or groove is provided between the pair of needle mount projections. The groove is dimensioned sufficiently small to enable wedging of needle in the groove between the needle mount projections, whereby the needle is releasably held stationary relative to the base by the needle mount 118.

A pair of needle guards 122 are secured to the base top surface 114 and project longitudinally above the base top surface on opposite sides of the needle mount 118. As seen in FIG. 10, the pair of needle guards 122 are spaced a sufficient distance above the base top surface 114 to enable the arms of the stitching instrument shown in FIG. 1, or the jaws of a surgical grasper, to pass between the needle guards 122 and the base top surface 114 when converging on the needle 116 held by the needle mount 118. This spacing of the needle guards provides sufficient access to the opposite ends of the needle so that the needle may be grasped by a surgical instrument, while also shielding the opposite ends of the needle held by the needle mount 118. The lateral spacing between the needle guards 122 is sufficient to enable the arms or jaws of a surgical instrument grasping the needle 116 to pass between the guards.

A suture holder 124 projects from the base top surface 114 adjacent the needle mount 118 and needle guards 122. The suture holder is basically comprised of a pair of adjacent panels 126 that project outwardly from the base top surface.

The panels 126 have a groove 128 therebetween that is dimensioned sufficiently small to hold portions of a length of suture 132 connected to the needle 116. As shown in FIG. 10, the portion of the suture length is overlapped several times and is wedged into the groove 128 between the panels 126. In this manner, the suture holder 124 releasably holds a short portion of the length of suture 132 adjacent the attachment of the suture to the needle 116.

The needle mount 118, needle guards 122 and suture holder 124 are all positioned on the base top surface 114 toward a distal end 134 of the magazine 110. The base proximal end 136 is formed as a connector 138 that attaches the magazine 110 to an elongate tube 142. The connector 138 is formed integrally with the base 112 and is connected to the base by a living hinge 144 that enables the connector 138 to pivot about the hinge 144 relative to the remainder of the base 112. A U-shaped channel 142 is formed extending longitudinally across the underside of the connector 138. The channel 146 has a lateral width open at the bottom of the connector and dimensioned sufficiently large to enable the channel to be either snap-fit or slidingly engaged over the exterior surface of the tube 142. The snap-fit or sliding engagement of the connector U-shaped channel 146 over the exterior surface of the distal end of the tube 142 provides a releasable connection between the base 112 at its proximal end to the tube 142 at its distal end. As the U-shaped channel extends longitudinally across the underside of the connector 138, it emerges through a circular opening 148 at the distal end 152 of the connector. The channel opening 148 is positioned adjacent a U-shaped groove 154 formed in the base top surface 114. As seen in FIG. 10, the top surface groove 154 extends longitudinally to a position adjacent the suture holder 124. As will be explained, the top surface groove 154 is dimensioned with a lateral width and longitudinal length sufficiently large to enable the distal end of a surgical instrument to pass through the groove to a position over the base top surface 114 where the pivoting arms or jaws of the instrument may close and grasp the ends of the needle 116 from the needle mount 118.

The elongate tube 142 extends from its distal end 156 received in the channel 146 of the connector 138 to a proximal end 158 of the tube. The tube proximal end has a circular handle or knob 162 formed thereon. The knob 162 has a notch 162 formed in its periphery that is dimensioned to receive the free end of the suture 132 wedged therein to hold the free end of the suture stationary relative to the proximal end of the tube. The tube 142 has an interior bore that extends between its opposite proximal and distal ends. The interior bore of the tube is dimensioned sufficiently large to enable a stitching instrument, surgical grasper or other surgical instrument to be passed entirely through the tube bore.

In use of the magazine and tube shown in FIG. 10 in loading a needle and length of suture formed in a knot loop onto a stitching instrument such as that shown in FIG. 1, the needle and length of suture must first be loaded onto the magazine. The needle is inserted between the projections of the needle mount 118 as shown in FIG. 10. These projections releasably hold the needle above the top surface 114 of the base. The length of suture extending from the needle is then overlapped on itself several times and inserted into the groove 128 between the panels 126 of the suture holder 124. From the suture holder 124, the suture then extends into the interior of the connector channel 146. There the suture is wrapped in at least one loop 166 over the exterior of the tube distal end 156 as shown in dotted lines in FIG. 10. Preferably, the pattern of the suture loop wrapped on the exterior surface of the tube is such that it will create a knot in the suture when the suture loop is pushed off the distal end of the tube and the needle 116, with suture attached, is passed through the loop as described in previous embodiments of the invention. From the suture loop 166, the suture then extends outside of the connector channel 146 and over the exterior surface of the tube 142 to the notch 164 in the tube handle 162 where the free end of the suture is releasably held.

In use of the magazine 112 with a stitching instrument 10 such as that shown in FIG. 1, the distal end of the instrument is first passed through the interior bore of the tube 142 until its arms 20, 22 are positioned on the opposite lateral sides of the needle 116 and the needle guards 122. The instrument handles are then manipulated to cause the arms to pivot toward each other and grasp the opposite ends of the needle 116 between the arms. The lateral length of the needle 116 prevents the instrument arms from engaging the opposite sides of the suture holder 124. The base distal end 134 is then pivoted about the living hinge 144 relative to the base proximal end 136 and the connector 138. This causes the instrument arms to pull the needle 116 from the needle mount 118 and pass between the needle guards. The magazine distal end 134 may then be downwardly pivoted further away from the instrument arms 120, 122 causing the suture holder 124 to clear the instrument arms and also causing the portion of the suture length held by the suture holder 124 to be pulled from its groove 128. The entire magazine may then be slipped longitudinally off of the distal end of the tube 156.

As the magazine 110 is moved axially off of the tube distal end 156, the slip-fit connection of the magazine connector 138 over the tube and the suture knot 166 causes the connector to pull the suture looped knot axially over the tube distal end 156 until the loop knot is moved onto the instrument distal end. With the magazine 110 completely removed from the distal end of the tube 142 and the distal end of the instrument, the relative positions of the instrument distal end, the tube distal end, the needle, suture and suture loop appear as shown in FIG. 11. The needle and suture are loaded on the instrument and are ready for making several stitching passes through body tissue. When the number of stitches desired is complete, the suture loop 166 may be passed off of the distal end of the instrument by reciprocating the tube 142 over the instrument distal end. The length of the suture attached to the needle 116 is then pulled through the suture loop 166 passed off the instrument end, thereby forming a knot in the suture in the same manner as previously described embodiments of the invention.

If the magazine 110 of FIG. 10 is to be employed with a conventional surgical grasper, it may be desirable to remove the needle guards 122 from the base top surface 114. This would facilitate removal of the needle from the needle mount 118 by the conventional grasper. However, most graspers will pass between the needle guards 122 while holding the needle 116. All other features of the magazine would remain the same.

FIGS. 12 and 13 show a further embodiment of the magazine 172 of the present invention. The magazine 172 of this embodiment is similar to the previously described embodiment and includes a base 174 having a longitudinal length and lateral width. The base top surface 176 is also provided with a needle mount 178, needle guards 182 and a first suture holder 184 that are substantially identical to the previously described embodiment of the magazine. Therefore, these features of the magazine 172 will not be described in further detail here.

The magazine 172 differs from the previously described embodiment in that it also includes a second suture holder 186 that is substantially identical to the first suture holder 184. The second suture holder is also provided with a pair of panels 188 that are spaced laterally from each other with a groove 192 formed between the panels. The groove 192 is dimensioned sufficiently small to enable an overlapped length of suture 194 to be wedged into the groove 192 and releasably held by the groove. In this embodiment, the suture 194 extends from the needle 196 held in the needle mount 178 to the first suture holder 184. A portion of the suture is overlapped on itself and is wedged in the groove of the first suture holder 184 where it is releasably held. The suture then extends to the second suture holder 186 where a portion of the suture is overlapped on itself and wedged in the second suture holder groove 192 where it is releasably held. From the second suture holder 186, the suture then extends back to the first suture holder 184 where a portion of its length is overlapped on itself and wedged in the first suture holder groove where it is releasably held. In this manner, a portion of a length of suture 194 adjacent its connection to the needle 196 is releasably held by the magazine 172.

From the first suture holder 184, the suture then extends to a suture mount 198 at the proximal end 202 of the magazine base 174. The suture mount in this embodiment of the magazine differs from that of the previously described embodiment. The suture mount is comprised of a pair of arms 204 that are spaced laterally from each other and project outwardly from the base proximal end 202. The lateral spacing between the pair of arms 204 is sufficiently large to enable insertion of a surgical instrument, such as the stitching device of FIG. 1 or a surgical grasper, through the lateral spacing. The arms each have a projection 206 intermediate their lengths. The arm projections 206 are positioned laterally opposite each other and each has an exterior surface 208. The length of suture 194 extending from the first suture holder 184 is wrapped in at least one loop 212 around the exterior surfaces 208 of the arm projections 206. In the preferred embodiment, the suture is wrapped in a loop that forms a knot in the length of suture as in previously described embodiments. To ensure that the suture loop 212 does not unintentionally slip off the arm projections 206, a pair of gates 214 are positioned longitudinally adjacent the arm projections 206 and engage against the projections. The gates 214 are resiliently attached to the base at its proximal end 202 and, due to the resiliency of the gates, may be manually pivoted away from the arm projections 206 to enable the suture loop 212 to be slipped off the exterior surfaces 208 of the projections. In their at rest positions, the resiliency of the gates 214 biases them into engagement with the arm projections 206 where the gates prevent the suture loop 212 from unintentionally slipping off the projection exterior surfaces 208.

From the suture loop 212 formed around the arm projections 206, the suture then extends to a spool 216 mounted for rotation to the bottom surface 218 of the magazine. The spool 216 is substantially identical to that of previously described embodiments of the magazine and stores the length of suture extending to the free end of the suture in the same manner as previous embodiments of the spool.

Figure 13A:
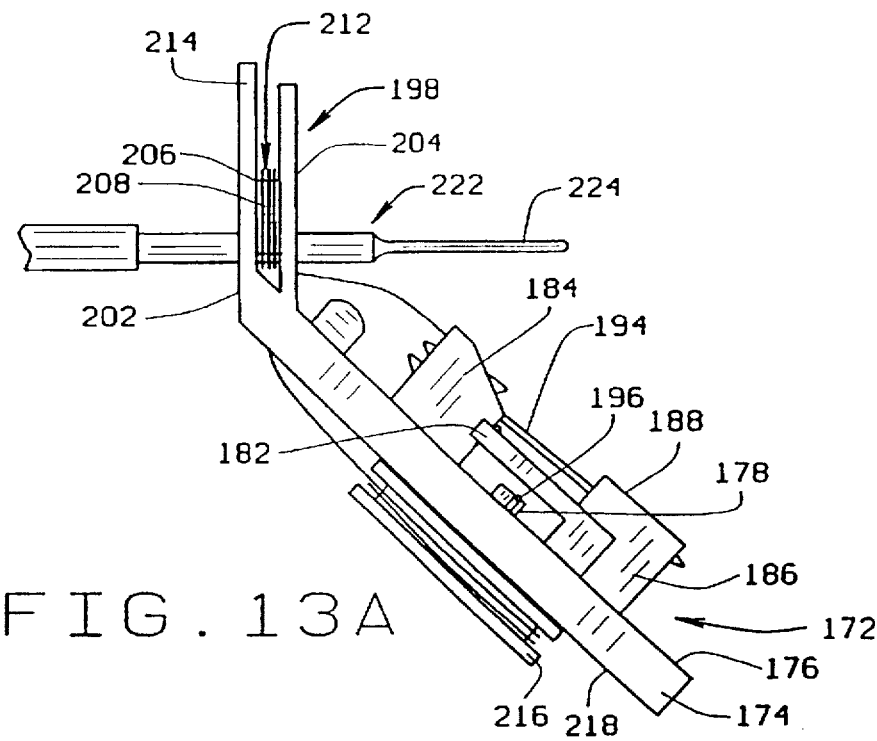
Figure 13B:
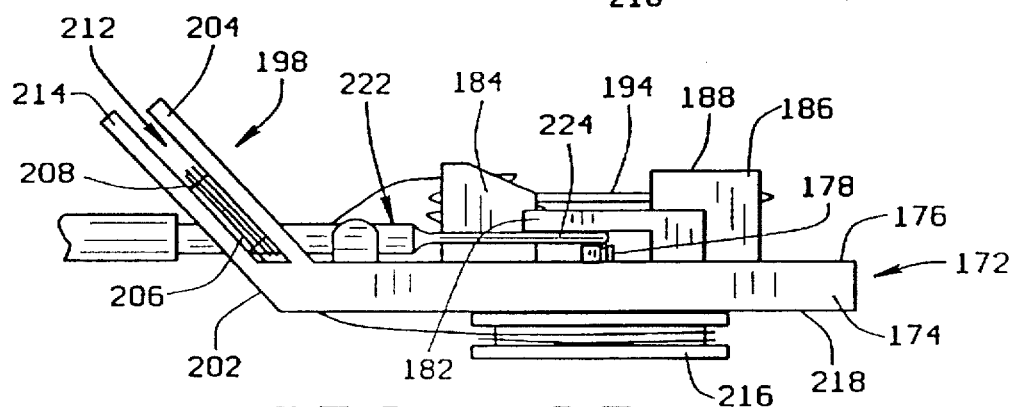
Figure 13C:
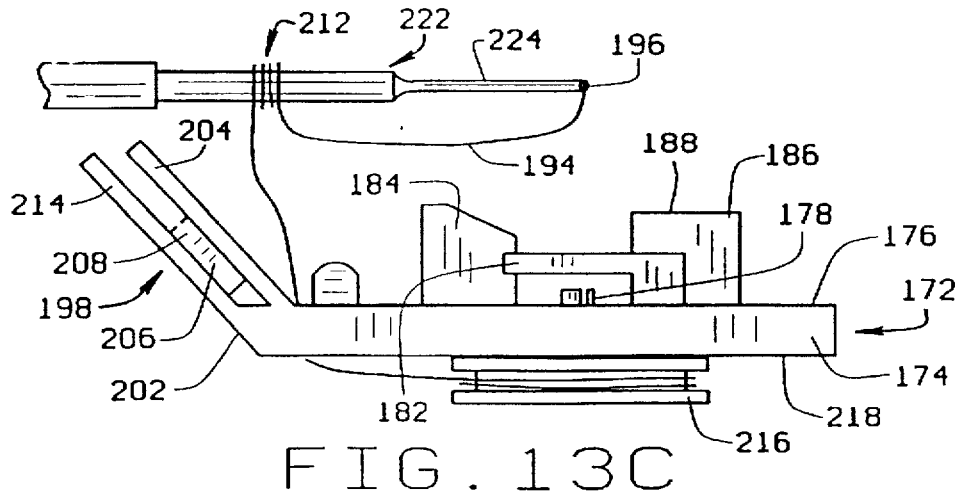

FIGS. 13A–13C illustrate the method of using the magazine of FIGS. 12 in loading a needle and length of suture onto a stitching instrument such as that shown in FIG. 1. The distal end 222 of the instrument is first inserted through the center of the suture loop 212 held on the arm projections 206. To facilitate insertion of the instrument through the loop, the magazine 172 is shown held relative to the instrument where the instrument distal end 222 is inserted axially along the center axis of the loop 212 formed in the suture on the arm projections. The magazine 172 is then pivoted upwardly so that the pivoting arms 224 are positioned on the opposite lateral sides of the needle guards 182. In this position, the instrument is manipulated so that the arms 224 pivot inwardly, grasping the ends of the needle 196 between the arms. With the needle held between the arms, the magazine is pivoted slightly downwardly causing the arms to lift and remove the needle 196 from the needle mount 178. The magazine may then again be pivoted further downwardly to substantially the same relative position shown in FIG. 13A to completely remove the needle 196 and the portion of the suture 194 adjacent the needle from the two suture holders 184, 198. Next, the pair of gates 214 are pivoted longitudinally away from the arm projections 206 to enable the loop of suture 212 to be slipped off the exterior surfaces 208 of the arm projections and onto the distal end of the instrument 222. This completes the loading of the needle and the suture loop onto the instrument. The magazine 172 may then be further separated from the surgical instrument 222 to cause the desired length of suture 194 to be spooled off of the spool 216 as shown in FIG. 13C. The free end of the suture may then be held by the surgeon or may be secured to an attachment of the surgical instrument as described with reference to the previous embodiments of the invention. The stitching instrument loaded with the needle and length of suture may then be used to form stitches in body tissue and tie a knot in the length of suture in the same manner as previously described embodiments.

As with the embodiment of FIG. 10A, if it is desired to use the magazine 172 of FIG. 12 with a surgical grasper, the needle guards 182 of the magazine may be removed to facilitate the removal of the needle from the magazine by the grasper.

While the present invention has been described by reference to specific embodiments, it should be understood that modifications and variations of the invention may be constructed without departing from the scope of the invention defined in the following claims.

What is claimed:

1. An apparatus for loading a needle onto a surgical instrument and for holding a length of suture attached to the needle, the apparatus comprising:

a needle and a length of suture attached thereto;

a base having opposite proximal and distal ends;

a needle mount on the base adjacent the distal end of the base, the needle mount having a configuration for holding the needle;

a suture mount on the base adjacent the proximal end of the base, the suture mount having a configuration for holding the length of suture attached to the needle and formed in a loop;

the needle mount and the suture mount being positioned relative to each other on the base to enable insertion of a surgical instrument through the loop of suture held by the suture mount and grasping of the needle held by the needle mount by the surgical instrument;

the base has a support surface extending across one side of the base, the needle mount is positioned to hold the needle above the support surface, and the suture mount is positioned to hold at least a portion of the loop of suture above the support surface.

2. The apparatus of claim 1, wherein:

the suture mount has a surface configured for holding the suture loop on the surface and for enabling sliding the suture loop off the surface and onto the surgical instrument inserted through the suture loop.

3. The apparatus of claim 1, wherein:

the suture mount has a pair of arms that project outwardly from the base and are spaced from each other a sufficient distance to enable insertion of the surgical instrument between the arms, and each of the arms has a surface thereon that is configured to hold a portion of the suture loop on the arm surface.

4. The apparatus of claim 1, wherein:

the needle mount holds the needle with at least one end of the needle projecting from the needle mount enabling the one end to be grasped by the surgical instrument and removed from the needle mount by the surgical instrument.

5. The apparatus of claim 1, wherein:

the needle mount has an opening therein and the needle is wedged in the opening for holding the needle on the needle mount.

6. The apparatus of claim 5, wherein:

the needle mount has a pair of projections and the opening is formed by a spacing between the projections, the spacing being sufficiently small to enable insertion and wedging of the needle in the spacing between the projections to hold the needle on the needle mount.

7. The apparatus of claim 1, wherein:

the suture mount holds the loop of suture on the base where the loop of suture can be removed from the suture mount by the surgical instrument inserted through the suture loop, and the needle mount holds the needle on the base where the needle can be removed from the needle mount by the surgical instrument.

8. An apparatus for loading a needle onto a surgical instrument and for holding a length of suture attached to the needle, the apparatus comprising:

a needle and a length of suture attached thereto;

a base having opposite proximal and distal ends;

a needle mount on the base adjacent the distal end of the base, the needle mount having a configuration for holding the needle;

a suture mount on the base adjacent the proximal end of the base, the suture mount having a configuration for holding the length of suture attached to the needle and formed in a loop;

the needle mount and the suture mount being positioned relative to each other on the base to enable insertion of a surgical instrument through the loop of suture held by the suture mount and grasping of the needle held by the needle mount by the surgical instrument;

the base has a support surface extending across one side of the base, the suture mount is positioned on the base to hold the suture loop about a center axis of the suture loop where the center axis extends over the support surface of the base, and the needle mount is positioned on the base to hold the needle positioned at an angle relative to the center axis of the suture loop.

9. The apparatus of claim 8, wherein:

the suture mount has a surface configured for holding the suture loop on the surface and for enabling sliding the suture loop off the surface and onto the surgical instrument inserted through the suture loop.

10. The apparatus of claim 8, wherein:

the suture mount has a pair of arms that project outwardly from the base and are spaced from each other a sufficient distance to enable insertion of the surgical instrument between the arms, and each of the arms has a surface thereon that is configured to hold a portion of the suture loop on the arm surface.

11. The apparatus of claim 8, wherein:

the needle mount holds the needle with at least one end of the needle projecting from the needle mount enabling the one end to be grasped by the surgical instrument and removed from the needle mount by the surgical instrument.

12. The apparatus of claim 8, wherein:

the needle mount has an opening therein and the needle is wedged in the opening for holding the needle on the needle mount.

13. The apparatus of claim 12, wherein:

the needle mount has a pair of projections and the opening is formed by a spacing between the projections, the spacing being sufficiently small to enable insertion and wedging of the needle in the spacing between the projections to hold the needle on the needle mount.

14. The apparatus of claim 8, wherein:

the suture mount holds the loop of suture on the base where the loop of suture can be removed from the suture mount by the surgical instrument inserted through the suture loop, and the needle mount holds the needle on the base where the needle can be removed from the needle mount by the surgical instrument.

15. An apparatus for loading a needle onto a surgical instrument and for holding a length of suture attached to the needle, the apparatus comprising:

a needle and a length of suture attached thereto;

a base having opposite proximal and distal ends;

a needle mount on the base adjacent the distal end of the base, the needle mount having a configuration for holding the needle;

a suture mount on the base adjacent the proximal end of the base, the suture mount having a configuration for holding the length of suture attached to the needle and formed in a loop;

the needle mount and the suture mount being positioned relative to each other on the base to enable insertion of a surgical instrument through the loop of suture held by the suture mount and grasping of the needle held by the needle mount by the surgical instrument;

the suture mount has a surface configured for holding the suture loop on the surface and for enabling sliding the suture loop off the surface and onto the surgical instrument inserted through the suture loop; and, the suture mount surface is configured for sliding the suture loop off the surface by sliding the suture loop away from the needle mount.

16. An apparatus for loading a needle onto a surgical instrument and for holding a length of suture attached to the needle, the apparatus comprising:

a needle and a length of suture attached thereto;

a base having opposite proximal and distal ends;

a needle mount on the base adjacent the distal end of the base, the needle mount having a configuration for holding a needle;

a suture mount on the base adjacent the proximal end of the base, the suture mount having a configuration for holding a length of suture attached to the needle and formed in a loop;

the needle mount and the suture mount being positioned relative to each other on the base to enable insertion of a surgical instrument through the loop of suture held by the suture mount and grasping of the needle held by the needle mount by the surgical instrument;

the suture mount has a surface configured for holding the suture loop on the surface and for enabling sliding the suture loop off the surface and onto the surgical instrument inserted through the suture loop; and, a gate is positioned adjacent the suture mount surface for preventing the suture loop from sliding off the surface, and the gate is operatively connected to the base for movement of the gate relative to the base and away from the suture mount surface to enable sliding of the suture loop off the suture mount surface.

17. A method of loading a length of suture formed in a loop onto a surgical instrument and for loading a needle attached to the length of suture onto the surgical instrument, the method comprising the steps of:

loading the surgical instrument from a magazine, the magazine having a suture mount holding the loop of the suture thereon, and the magazine having a needle mount holding the need thereon;

loading the suture loop on the surgical instrument by inserting the surgical instrument through the suture loop held on the suture mount;

loading the needle on the surgical instrument by grasping the needle held on the needle mount with the surgical instrument;

the loop of suture is loaded on the surgical instrument by sliding the loop of suture off the suture mount and onto the surgical instrument and the needle is loaded onto the surgical instrument by pulling the needle from the needle mount with the surgical instrument.

18. The method of claim 17, wherein:

the needle is grasped from the needle holder by the surgical instrument with the surgical instrument inserted through the suture loop.

* * * * *